(12) United States Patent
Nilsson

(10) Patent No.: US 8,140,158 B2
(45) Date of Patent: Mar. 20, 2012

(54) HEART MONITORING DEVICE AND A SYSTEM TO DETECT VIBRATIONS CONCERNING THE STATUS OF THE HEART

(75) Inventor: Kenth Nilsson, Åkersberga (SE)

(73) Assignee: St. Jude Medical AB, Jarfalla (SE)

( * ) Notice: Subject to any disclaimer, the term of this patent is extended or adjusted under 35 U.S.C. 154(b) by 873 days.

(21) Appl. No.: 11/916,461

(22) PCT Filed: Jun. 16, 2005

(86) PCT No.: PCT/SE2005/000946
§ 371 (c)(1),
(2), (4) Date: Jul. 16, 2008

(87) PCT Pub. No.: WO2006/135294
PCT Pub. Date: Dec. 21, 2006

(65) Prior Publication Data
US 2008/0269820 A1    Oct. 30, 2008

(51) Int. Cl.
*A61N 1/365* (2006.01)
(52) U.S. Cl. .................. 607/18; 607/2; 607/17; 600/508

(58) Field of Classification Search ............... 607/17–18
See application file for complete search history.

(56) References Cited

U.S. PATENT DOCUMENTS

| 4,101,795 | A | * | 7/1978 | Fukumoto et al. ............ 310/336 |
| 4,771,792 | A | | 9/1988 | Seale |
| 5,305,745 | A | * | 4/1994 | Zacouto ........................ 600/324 |
| 5,447,523 | A | | 9/1995 | Schaldach |
| 6,044,299 | A | | 3/2000 | Nilsson |
| 2005/0027323 | A1 | | 2/2005 | Mulligan et al. |
| 2006/0265020 | A1 | * | 11/2006 | Fischell et al. .................. 607/30 |

* cited by examiner

*Primary Examiner* — Carl H Layno
*Assistant Examiner* — Paula J Stice
(74) *Attorney, Agent, or Firm* — Schiff Hardin LLP

(57) ABSTRACT

An implantable heart monitoring system has a control circuit that operates an implanted vibrator to emit a vibration signal that interacts with tissue in vivo. A vibration sensor detects vibrations after interaction with the tissue, and supplies a detection signal to the control circuit. The control circuit analyzes the vibrations in the detected signal relative to the vibration signal, and derives information concerning at least one mechanical property of the heart therefrom, such as stiffness and/or thickness of at least a part of the heart.

23 Claims, 3 Drawing Sheets

HEART MONITORING DEVICE AND A SYSTEM TO DETECT VIBRATIONS CONCERNING THE STATUS OF THE HEART

BACKGROUND OF THE INVENTION

1. Field of the Invention

The present invention relates to an implantable heart monitoring device which is able to detect vibrations in order to obtain information concerning the heart.

The invention also relates to a system including such a device and to the use of the system. The device may be used to monitor the status of a heart of a human or animal being as well as to stimulate said heart.

2. Description of the Prior Art

Several different implantable devices for monitoring and stimulating a heart are known.

U.S. Pat. No. 6,044,299 describes an implantable medical device that has a housing containing an accelerometer which detects vibrations of the housing. The accelerometer generates a signal in response to the detected vibrations, which is supplied to a signal processing unit. The signal processing unit generates, for each of a number of pre-determined frequency ranges, a parameter value indicative of a defined attribute of the signal. The signal processing unit forms a ratio between any two of these parameter values, and emits at least one status value dependent on this ratio. The status value is uniquely indicative of a predetermined type or level of cardiac activity, and the status values can be used as a control signal for controlling therapy, such as cardiac stimulation, administered by the implantable medical device.

United States Patent Application Publication 2005/0027323 describes a device for monitoring cardiac blood pressure and chamber dimension. The dimension sensor or sensors comprise at least a first sonomicrometer piezoelectric crystal mounted to a first lead body implanted into or in relation to one heart chamber that operates as an ultrasound transmitter when a drive signal is applied to it and at least one second sonomicrometer crystal mounted to a second lead body implanted into or in relation to a second heart chamber that operates as an ultrasound receiver. The time delay between the generation of the transmitted ultrasound signal and the reception of the ultrasound wave varies as a function of distance between the ultrasound transmitter and receiver which in turn varies with contraction and expansion of a heart chamber between the first and second sonomicrometer crystals.

U.S. Pat. No. 4,771,792 describes a non-invasive system and method for inducing vibrations in a selected element of the human body and detecting the nature of responses for determining mechanical characteristics of the element. In particular an internal pressure of the selected body element is determined.

SUMMARY OF THE INVENTION

An object of the invention is to provide an implantable heart monitoring device which makes it possible to obtain information concerning the status of the heart. A further object is to provide such a device which with relatively simple means makes it possible to obtain such status information. Further objects and advantages of the invention will become clear from the below description and claims.

The above objects are achieved by an implantable heart monitoring device having a housing and a control circuit located within said housing. The control circuit is arranged to generate a vibration signal suitable to actuate a vibrator which constitutes a built-in vibrator which forms part of the implantable heart monitoring device or which constitutes an implantable vibrator which does not form part of the device itself but which communicates with the device. The vibration signal is able to cause the vibrator to vibrate. The control circuit is also adapted to communicate with at least a first implantable vibration sensor suitable to be arranged in or at the heart of a living being, wherein the control circuit is arranged to receive a detection signal from said vibration sensor, which detection signal represents the detected vibration. The control circuit is also arranged to carry out a procedure that involves the generation of at least one vibration signal and the detection of at least one detection signal, receivable from first vibration sensor, indicating a vibration sensed in response to a vibration delivered by the vibrator in response to the vibration signal. The control circuit is arranged to be able to derive, based on the received detection signal in relation to the generated vibration signal, information concerning the mechanical properties of the heart, such as the stiffness and/or the thickness of at least a part of the heart.

By using a vibrator and a vibration sensor as described above, it is thus possible to obtain information concerning the mechanical properties of the part of the heart that is positioned between the vibrator and the vibration sensor. The present invention can thus be used to monitor the status of the heart. In particular, it is possible to monitor the heart muscle and/or heart tissue condition with the help of the present invention. A change in the heart muscle or tissue status may be caused by different factors, such as by an infarct or ischemia. It is important to be able to detect such change in the status of the heart. This is possible with the present invention since the invention provides information concerning the mechanical properties of the heart.

In an embodiment of the device according to the invention, the control circuit is arranged such that said procedure involves deriving a mechanical transfer function, which represents the mechanical properties between the vibrator and the vibration sensor. The mechanical transfer function can be seen as a function that represents how the mechanical properties between the vibrator and the vibration sensor influences the signal between the vibrator and the vibration sensor. The mechanical transfer function thus provides information concerning the mechanical properties of the heart, or the part of the heart that is located between the vibrator and the vibration sensor.

According to a further embodiment of the device according to the invention, the device has at least one memory connected to the control circuit, and the control circuit is arranged to be able to operate in time cycles corresponding to heart cycles. The control circuit is arranged to carry out the procedure at a number of occasions, with several time cycles between each occasion, and to store a result from the procedure in the memory, such that information is derived as to how the mechanical properties of the heart have changed between these occasions. An important aspect of the invention is to monitor how the mechanical properties of the heart changes over time. It is for example important for a physician to be able to monitor the progression of a heart disease in order to be able to apply a suitable therapy to the patient. The time between each occasion, when the heart status is checked with the help of the device, can preferably be several hours or even several days. It should be noted that at each occasion, it is possible to carry out the mentioned procedure several times, in order to have a good statistical basis for the heart condition. The information concerning the mechanical properties of the heart that is obtained at a certain occasion can thus constitute, for example, an average result of several procedures carried out soon after each other.

In a further embodiment of the device according to the invention, the control circuit is arranged such that said procedure is carried out at the same portion of said time cycle at the different occasions. In order to be able to compare the status of the heart at different occasions, it is advantageous if the procedure is carried out during the same portion of a heart cycle, for example during a certain portion of the diastolic phase.

In a further embodiment of the device according to the invention, the control circuit is arranged such that said procedure includes the delivery of signals generating vibrations of at least two different frequencies and receiving corresponding detection signals. A change in the heart condition (for example if a heart wall has become more stiff) will influence signals of different frequencies to different degrees. Therefore, by comparing the signals detected at two different frequencies, accurate information concerning the mechanical properties of the heart can be obtained. It is of course also possible to use more than two different frequencies. The frequencies can for example be somewhere between 10 Hz and 1000 Hz, preferably between 50 Hz and 250 Hz.

According to a further embodiment of the device according to the invention, the control circuit is arranged such that said procedure includes the determination of the amplitude of the detection signal or signals. The amplitude of the detection signal indicates how much the signal has been attenuated between the vibrator and the vibration sensor and thus provides information concerning the mechanical properties of the heart. In particular, if the procedure involves signals of different frequencies, the control circuit can compare the amplitudes in the detected signals of the different frequencies.

In a further embodiment of the device according to the invention, the control circuit is arranged such that said procedure includes the determination of the phase angle between the vibration signal and the corresponding detection signal. This phase angle includes information of how much the detection signal is delayed compared to the vibration signal. Thus also this phase angle provides information concerning the mechanical properties between the vibrator and the vibration sensor.

In a further embodiment of the device according to the invention, the control circuit is arranged such that said procedure includes the determination of the energy of the vibration detected through the detection signal or signals. By determining the energy of the sensed vibration, information is obtained of how much energy has been absorbed between the vibrator and the vibration sensor. Thereby information concerning the mechanical properties of the heart is obtained.

In a further embodiment of the device according to the invention, the control circuit is arranged such that said procedure includes the generation of said vibration signal in the form of a short burst, and the determination of the time it takes from the generation of the vibration signal to the detection of the corresponding detection signal. By detecting the time it takes for the signal to reach the vibration sensor, information can be obtained of the distance between the vibrator and the vibration sensor. This time can also include information concerning for example the thickness of a heart wall located between the vibrator and the vibration sensor.

According to a further embodiment of the device according to the invention, the control circuit is arranged such that said procedure includes the detection of the morphology of the detection signal or signals. The morphology, or, in other words, "the shape", of the detected signal provides information concerning the mechanical properties between the vibrator and the vibration sensor. It is for example possible that the vibration signal has the shape of a square pulse and that the morphology of the corresponding detection signal is analyzed.

According to a further embodiment of the device according to the invention, the vibrator constitutes a built-in vibrator which forms part of the implantable heart monitoring device. The invention can be implemented in a simple manner if the vibrator is built-in in the implantable device. It is however also possible that the vibrator is for example positioned on a lead that is connected to the device.

According to a further embodiment of the device according to the invention, the device has a second vibration sensor, located within said housing and connected to the control circuit such that the control circuit receives a detection signal from said second vibration sensor, which detection signal represents the vibration of the housing. By arranging a vibration sensor in the housing, it is possible to sense the vibration of the housing.

In a further embodiment of the device according to the invention, the control circuit is arranged such that the procedure includes comparing the detection signals from the first and second vibration sensors. According to this embodiment, it is thus possible to compare the vibration of the housing with the vibration detected by the first vibration sensor. It is thereby possible to obtain information of how the mechanical properties between the housing and the first vibration sensor influence the signal.

In a further embodiment of the device according to the invention, the device includes a detector arranged to indicate when a patient in whom the device is implanted is likely to be at rest, wherein the control circuit is arranged such that the procedure is carried out when said detector indicates that the patient is likely to be at rest. A more accurate indication of the heart status can be obtained if the procedure is carried out when the patient is resting. The procedure may for example be carried out when the patient is asleep.

In a further embodiment of the device according to the invention, the control circuit is arranged to, under certain conditions, be able to generate an alarm signal in order to alert a patient carrying the implanted device, and the device is arranged such that the alarm signal causes the vibrator to vibrate with such an intensity and duration, that a patient in whom the device is implanted will be alerted. It is known that an implantable heart stimulating device can include a vibrator that may alert the patient. According to this advantageous embodiment of the present invention, the vibrator in question, which may either be built-in or external to the device, can be used both to generate an alarm signal and to generate the vibration signal that is used in the procedure for determining the status of the heart.

In a further embodiment of the device according to the invention, the device also includes means for delivering pacing pulses to one or more electrode surfaces adapted to stand in communication with the device and suitable to be positioned in or at the heart of a living being, such that pacing pulses can be delivered to said heart. According to this embodiment, the device also constitutes a heart stimulating device and can thus be used to stimulate the heart. The device may of course also include means for sensing the electrical activity of the heart, which is common in this technical field.

Another aspect of the invention relates to an implantable heart monitoring system. According to the invention, this system includes a heart monitoring device according to any one of the preceding embodiments, and at least said first implantable vibration sensor, wherein said control circuit is arranged to communicate with said first implantable vibration sensor.

According to an embodiment of the system according to the invention, the system also includes the implantable vibrator, which does not form part of the device, and the control circuit is arranged to communicate with the implantable vibrator.

With the heart monitoring system according to the invention, advantages corresponding to those mentioned above in connection with the device are obtained.

Another aspect of the invention relates to a use of the system according to the invention. According to this use, the system is implanted in a living being and said first implantable vibration sensor is positioned in or at the heart of said living being.

According to one manner of using the system, also the implantable vibrator, which does not form part of the device, is positioned in or at the heart of said living being.

The system can be used to determine the condition of the heart muscle and/or heart tissue of a patient in which the device is implanted.

The system can be used to determine the condition of the heart in a patient suffering from congestive heart failure.

With the manners of using the system according to the invention, the status of the heart of an actual patient is thus obtained.

DESCRIPTION OF THE PREFERRED EMBODIMENTS

Figure 1:
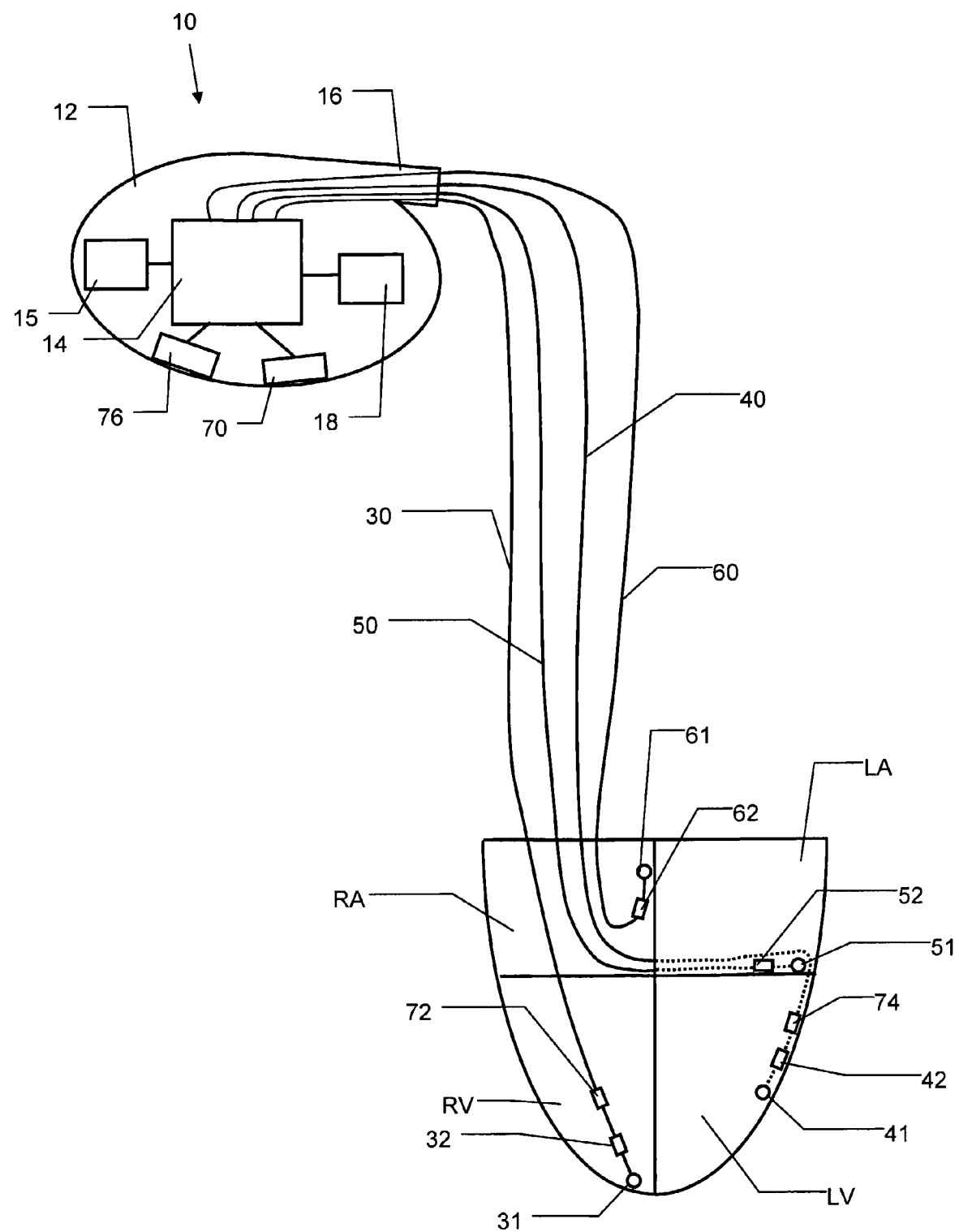
FIG. 1 schematically illustrates an exemplary embodiment of a device and system in accordance with the present invention.

FIG. 1 shows schematically an implantable heart monitoring device 10 according to the invention. According to the embodiment illustrated in FIG. 1, the device 10 is not only arranged to monitor a heart but also to be able to stimulate a heart, i.e. to deliver pacing pulses. The device 10 has a housing 12. Inside the housing 12 a control circuit 14 is arranged. The device 10 may constitute a pacemaker which is also able to detect electrical signals from a heart. Since such a device is well known to a person skilled in the art, the details of this device will not be described more closely here. The device comprises a connector portion 16. Different leads 30, 40, 50, 60 may be connected to the control circuit 14 via the connector portion 16.

The control circuit 14 can be seen to include all the different means necessary for delivering pacing pulses and for sensing the electrical activity of a heart. The control circuit 14 can thus include all the different means which are normal in heart pacemakers. The control circuit 14 is thus arranged to be able to operate in time cycles corresponding to heart cycles. The device also includes a memory 15 connected to the control circuit 14. Furthermore, the device includes an activity sensor 18, connected to the control circuit 14, which indicates the activity of a patient in whom the device is implanted. The activity sensor 18 can thus indicate when the patient in question is resting.

Furthermore, according to the embodiment shown in FIG. 1, the device 10 includes a vibrator 70 located within the housing 12. The vibrator 70 is connected to the control circuit 14. The control circuit 14 can generate a vibration signal which causes the vibrator 70 (and thereby the device 10) to vibrate. The vibrator can include, for example, a piezoelectric crystal which vibrates in response to the vibration signal. Under certain conditions, the control circuit 14 can also generate an alarm signal which causes the vibrator 70 to vibrate with a sufficient intensity and duration, such that a patient in whom the device 10 is implanted will be alerted. The vibrator 70 can thus also be used to generate a warning signal to the patient.

In the shown embodiment, the device 10 also includes a vibration sensor 76 located within the housing 12 and connected to the control circuit 14. The vibration sensor 76 senses the vibration of the device 10. The control circuit 14 thus receives a detection signal from the vibration sensor 76, which detection signal represents the vibration of the housing 12.

In the shown embodiment, four leads 30, 40, 50, 60 are connected to the device 10. The first lead 30 includes electrode surfaces 31, 32. The electrode surface 31 can be called a tip electrode. The electrode surface 32 can be called a ring electrode. The electrode surfaces 31 and 32 together thus constitute a bipolar electrode. Corresponding electrode surfaces 41, 42, 51, 52, 61, 62 are arranged on the leads 40, 50, 60, respectively.

As is well known to a person skilled in the art, unipolar electrodes can be used instead of bipolar electrodes. Furthermore, the numbers of leads 30, 40, 50, 60 can depend on the purpose of the device 10.

FIG. 1 also schematically illustrates a heart with a right atrium RA, a right ventricle RV, a left atrium LA and a left ventricle LV. The bipolar electrode 31, 32 is positioned in the right ventricle RV. The bipolar electrode 61, 62 is positioned in the right atrium RA. The bipolar electrode 51, 52 is positioned in the coronary sinus, and can thus sense and stimulate the left atrium LA. The bipolar electrode 41, 42 has been introduced via the coronary sinus into a cardiac vein. The bipolar electrode 41, 42 can be used to sense and stimulate the left atrium LV.

The lead 30 also includes a vibrator 72 positioned in the right ventricle RV. The vibrator 72 thus constitutes an implantable vibrator 72 which does not form part of the device 10 itself but which communicates with the device 10 via the lead 30. The vibrator 72 can include, for example, a piezoelectric crystal that vibrates in response to a vibration signal from the control circuit 14.

The lead 40 also includes a vibration sensor 74. According to the shown embodiment, this vibration sensor is located in a cardiac vein close to the left ventricle LV. The control circuit 14 can thus receive a detection signal from the vibration sensor 74, which detection signal represents the detected vibration. The vibration sensor 74 can include a piezoelectric crystal that senses vibrations. The vibration sensor 74 can be sensitive to acceleration, sound, displacement, velocity or pressure.

It can be noted that the device 10 together with the leads 30, 40, 50, 60, the electrodes 31, 32, 41, 42, 51, 52, 61, 62 and the vibrator 72 and the vibration sensor 74 constitute an embodiment of a system according to the invention. It should also be noted that the number of vibration sensors 74, 76 and vibrators 70, 72 can vary. Furthermore, the vibration sensor 74 could be positioned in other positions in or at the heart than in the position shown in FIG. 1. Moreover, the vibrator 72 could be positioned in other positions in or at the heart. Furthermore, according to one embodiment it is sufficient to use the built-in vibrator 70 and thus not necessary to have any vibrator 72 in the heart.

According to the present invention, the control circuit 14 is arranged to carry out a procedure for deriving information concerning the mechanical properties of the heart, such as the stiffness and/or the thickness of at least a part of the heart. This procedure involves the generation of a vibration signal with the help of the control circuit 14. The vibration signal causes a vibrator 70 or 72 to vibrate. The vibration sensor 74 senses the vibration and the control circuit 14 receives a detection signal from the vibration sensor 74. Since heart tissue is located between the vibrator 70 or 72 and the vibration sensor 74, the vibration sensed by the vibration sensor 74 depends on the properties of the portion of the heart that is located between the vibrator 70 or 72 and the vibration sensor 74. The following relationship can be considered:

(sensed vibration)=$f$(generated vibration)

The sensed vibration is thus a function $f$ of the generated vibration. The function $f$ can be seen as a mechanical transfer function. The mechanical transfer function $f$ thus depends on the mechanical characteristics between the vibrator 70 or 72 and the vibration sensor 74.

Figure 2A:
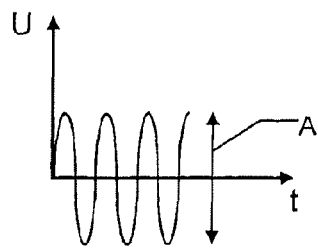
FIGS. 2A and 2B respectively schematically illustrate a first example of a vibration signal and a detection signal resulting therefrom, in accordance with the present invention.
Figure 2B:
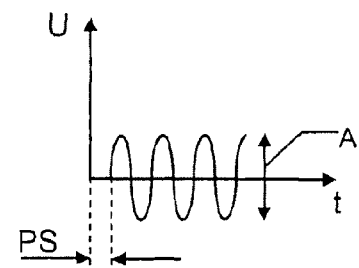

FIG. 2A shows schematically an example of a vibration signal generated by the control circuit 14. The X-axis represents the time t and the Y-axis represents a voltage U. FIG. 2B illustrates schematically the corresponding detection signal received by the control circuit 14 from the vibration sensor 74. In the figures, A represents the amplitude of the respective signal and PS represents the phase shift in the detection signal, i.e. the phase angle between the vibration signal and the corresponding detection signal. The phase shift PS thus represents the time delay between the vibration signal and the detection signal. This time delay PS depends on the distance between the vibrator 70 or 72 and the vibration sensor 74 as well as on the material between the vibrator 70 or 72 and the vibration sensor 74. The difference in amplitude A between the detection signal and the vibration signal provides information about the attenuation of the signal between the vibrator 70 or 72 and the vibration sensor 74. The control circuit 14 preferably includes suitable filter means such that vibrations that are not caused by the generated vibration signal are filtered out when the detection signal is analysed. Since the vibration signal or signals are generated by certain frequencies, it is quite easy to filter out signals that are not to be taken into account when analysing the signal from the vibration sensor 74 (and 76).

Figure 3A:
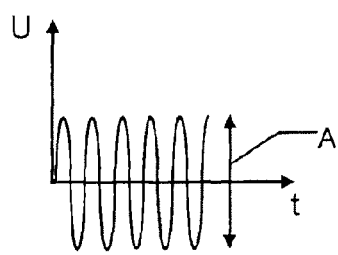
FIGS. 3A and 3B respectively schematically illustrate a second example of a vibration signal and a detection signal resulting therefrom, in accordance with the present invention.
Figure 3B:
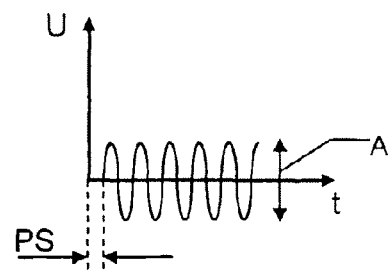

FIGS. 3A and 3B discloses similar signals to those of FIGS. 2A and 2B. However, the vibration signal represented in FIG. 3A has a higher frequency than the signal in FIG. 2A. Consequently, the detection signal of FIG. 3B also has the same, higher frequency as the signal in FIG. 3A. The attenuation, i.e. the amplitude A of the detection signal relative to the vibration signal can depend on the frequency. Furthermore, the relationship between the amplitudes A detected at different frequencies depends on the physical matter between the vibrator 70 or 72 and the vibration sensor 74. Consequently, by generating vibration signals of different frequencies and by detecting the corresponding detection signals, information about the mechanical properties of the heart can be obtained.

Figure 4A:
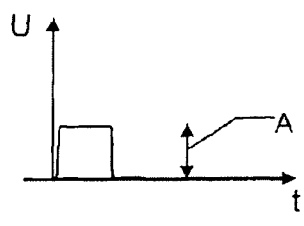
FIGS. 4A and 4B respectively schematically illustrate a third example of a vibration signal and a detection signal resulting therefrom, in accordance with the present invention.
Figure 4B:
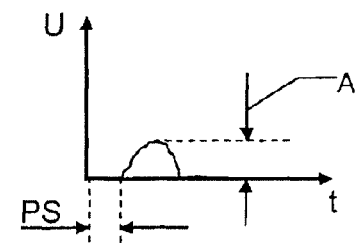

FIG. 4A illustrates schematically another kind of vibration signal. In this case the signal has the form of a square pulse. FIG. 4B represents the corresponding detection signal. As in connection with the previous figures, the amplitude A and the phase shift PS provides information concerning the properties between the vibrator 70 or 72 and the vibration sensor 74. Also the morphology (the shape) of the detection signal can provide information concerning the mechanical properties of the heart.

The duration of the generated vibration signal can be long or short. It is for example possible to generate a vibration signal in the form of a short burst, which has a duration of for example less than 50 ms, or preferably less than 20 ms. The control circuit 14 can then be arranged to detect the time it takes from the generation of this vibration signal until the detection of the corresponding detection signal.

It is also possible to analyse the energy of the detection signal. The energy can be represented with (or is at least proportional to) the following integral:

$$\int_{t_1}^{t_2} U^2(t)\,dt$$

where U is the voltage, t is the time, $t_1$ is the time at the beginning of the signal and $t_2$ is the time at the end of the signal. The total energy in the detection signal thus depends on the mechanical properties of the part of the heart located between the vibrator 70 or 72 and the vibration sensor 74.

It should be noted that although it may be difficult to obtain any exact information concerning the mechanical properties of the heart from a single measurement, it is an important aspect of the invention that the change of the status of the heart over a longer time can be detected quite accurately with the help of the present invention. Therefore, the mentioned procedure is preferably carried out at a plurality of occasions, for example once a day, once a week or once a month. At each occasion the result of the procedure is stored in the memory 15. It is thereby possible to derive information of how the mechanical properties of the heart have changed between the occasions.

Preferably, the procedure is carried out when the patient in whom the system is implanted is resting. This can be indicated with the help of the activity sensor 18 mentioned above.

If the built-in vibrator 70 is used as the vibrator, it is possible to sense the vibration of the device 10 with the help of the built-in vibration sensor 76. It is thereby possible to compare the vibration sensed by the vibration sensor 76 with the vibration sensed by the vibration sensor 74. The comparison can be done in similar manners to those described above in connection with FIG. 2-4. In this case, the vibration sensed by the vibration sensor 76 can be seen to be represented in the FIGS. 2A, 3A and 4A.

Preferably, the mentioned procedure for determining the mechanical properties of the heart is carried out during a small portion of the heart cycle, for example during a time period of less than 100 ms, or preferably less than 50 ms. It is advantageous to perform the procedure during a short time such that the heart does not have time to change its shape too much during the procedure (the shape of the heart of course changes during each heart beat). Furthermore, it is preferred that the procedure is carried out at the same portion of different heart cycles, for example during the diastolic phase. This makes it easier to compare the measurements done at different occasions.

Figure 5:
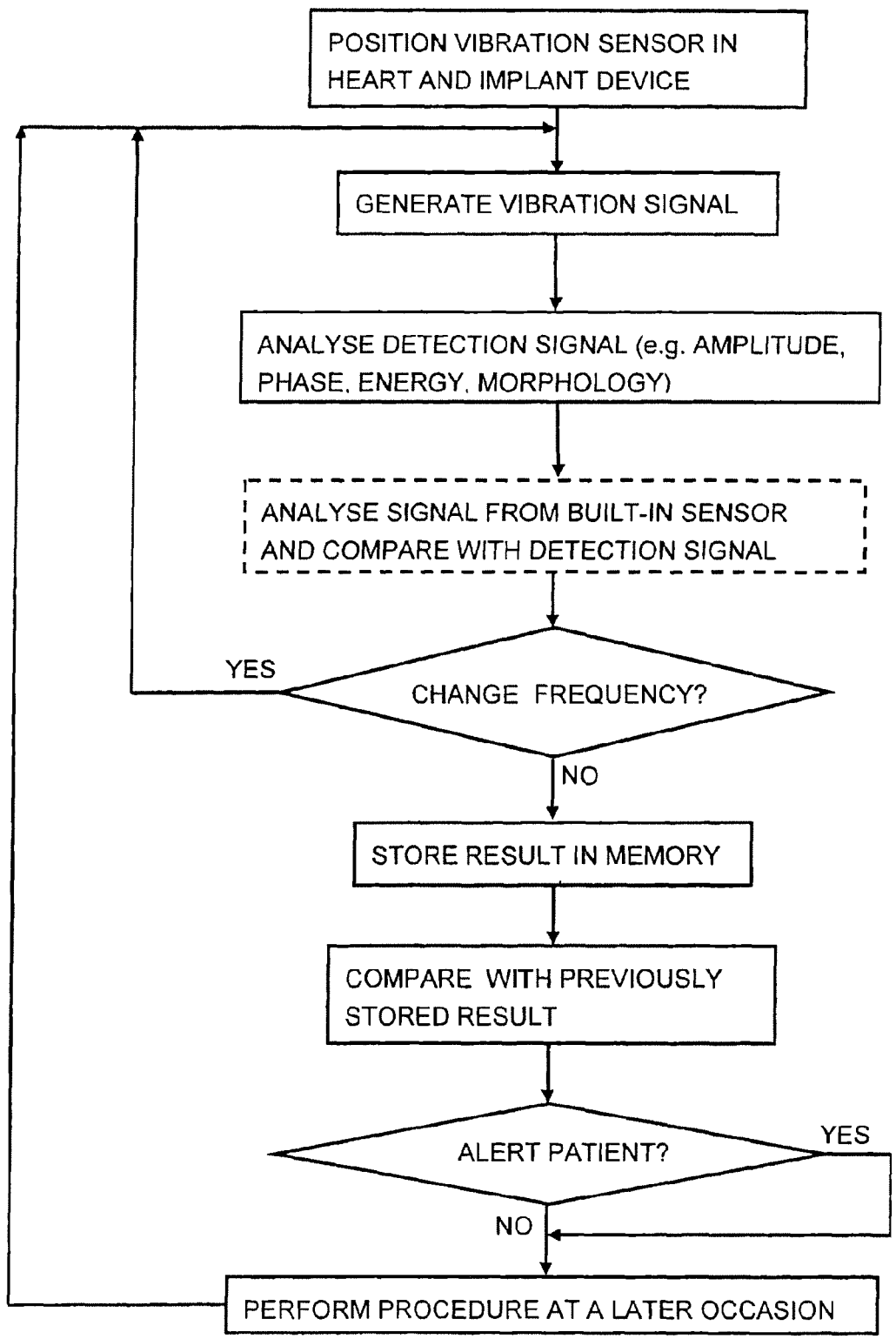
FIG. 5 is a flow chart describing an example of operation of the device and system in accordance with the present invention.

FIG. 5 illustrates schematically a manner of using the system according to the invention and at the same time schematically the manner in which the device operates. The system according to the invention is thus used such that the leads 30, 40, 50, 60 with the electrodes 31, 32, 41, 42, 51, 52, 61, 62 and the vibrator 72 and the vibration sensor 74 are introduced into the heart of a patient. Furthermore, the leads 30, 40, 50, 60 are connected to the device 10 and the device is implanted in the patient. The system according to the invention is with advantage used in a patient suffering from congestive heart failure. The system can be used to determine the condition of the heart muscle and/or heart tissue of at least a portion of the heart of the patient. In particular, the system is used to monitor how this condition changes over time.

The device operates by generating a vibration signal during a certain portion of a heart cycle. The corresponding detection signal is detected and analysed. This analysis may include for example the amplitude, the phase, the energy and/or the morphology of the detection signal.

According to one embodiment of the invention, also the signal from a built-in vibration sensor 76 is detected and the detection signal from the vibration sensor 74 is compared with the vibration signal from the built-in vibration sensor 76.

Thereafter the frequency can be changed such that a new vibration signal of another frequency is generated. The corresponding detection signal is analysed. The frequency could be changed once, so that vibrations of two different frequencies are generated. However, it is also possible to change the frequency more than once during the procedure, such that vibration signals of more than two different frequencies are generated.

The relevant information from this procedure is stored in the memory 15. At a later occasion (for example a day later) the same procedure is carried out again and also the new result is stored in the memory. The new result can be compared with the old result stored in the memory in order to provide information concerning the change of the heart status. If the status of the heart has changed to for the worse, it is possible to generate an alarm signal in order to alert the patient. Another possibility is to change some pacing parameter in order to improve the function of the heart.

Although modifications and changes may be suggested by those skilled in the art, it is the intention of the inventors to embody within the patent warranted heron all changes and modifications as reasonably and properly come within the scope of their contribution to the art.

I claim as my invention:

1. An implantable heart monitoring system comprising:
a housing configured for implantation in a subject;
a vibrator configured for implantation in the subject and operable to emit a vibration signal from a first in vivo site into cardiac tissue exhibiting a tissue transfer function representing physical properties of the cardiac tissue in the subject;
a vibration sensor configured for implantation at a second in vivo site in the subject, said vibration sensor configured to detect said vibration signal after said vibration signal has propagated through said tissue between said first in vivo site and said second in vivo site and is further configured to emit a detection signal that represents the detected vibrations; and
a control circuit in said housing in communication with said vibrator and said vibration sensor, said control circuit being configured to execute a procedure comprising actuating said vibrator to emit said vibration signal and receiving said detection signal from said vibration sensor, and to derive based on the detected vibrations in relation to the vibration signal said tissue transfer function, and to derive from said tissue transfer function, information describing at least one medical property of the heart of the subject, selected from the group consisting of stiffness of a heart portion of the heart and a thickness of a portion of the heart.

2. A system as claimed in claim 1 wherein said vibrator is located outside of said housing and is separately implantable in the subject.

3. A system as claimed in claim 2 wherein said vibration sensor is built into said housing.

4. A system as claimed in claim 1 wherein said vibrator is built into said housing.

5. A system as claimed in claim 1 wherein said vibration sensor is located outside of said housing and is separately implantable in the subject.

6. A system as claimed in claim 1 wherein said control circuit, in said procedure, derives a mechanical transfer function representing mechanical properties of in vivo tissue between said vibrator and said vibration sensor, as said information.

7. A system as claimed in claim 1 comprising a memory in communication with said control circuit, and wherein said control circuit is operable in time cycles corresponding to heart cycles of the heart, and wherein said control circuit executes said procedure a plurality of times, with a plurality of time cycles between each execution, and stores a result from each execution of the procedure in the memory, as respective stored results, and derives said information based on a change between successive stored results.

8. A system as claimed in claim 7 wherein said control circuit executes said procedure in a same portion of each time cycle in which the procedure is executed.

9. A system as claimed in claim 1 wherein said control circuit operates said vibrator to emit respective vibration signals having at least two different frequencies, and wherein said vibration sensor discriminates between said two different frequencies in said detection signal.

10. A system as claimed in claim 1 wherein said control circuit derives said information from a characteristic of the detected vibrations in said detection signal selected from the group consisting of amplitude, phase angle, energy content and morphology.

11. A system as claimed in claim 1 wherein said control circuit operates said vibrator to emit said vibration signal as a short burst, and derives said information from a determination of a time beginning from emission of the vibration signal to detection of said detection signal.

12. A system as claimed in claim 1 wherein said vibration sensor is a first vibration sensor implanted separate from said housing, and wherein said system comprises a second vibration sensor built into said housing and connected to said control circuit, and wherein said second vibration sensor emits a further detection signal representing vibration of the housing, and wherein said control circuit derives said information based on said detection signal from said first vibration sensor and said further detection signal from said second vibration sensor.

13. A system as claimed in claim 12 wherein said control circuit derives said information by comparing said detection signal and said further detection signal.

14. A system as claimed in claim 1 comprising a posture detector in said housing that detects when the subject is likely to be at rest, and wherein said control circuit executes said procedure only when said posture detector indicates that the subject is likely to be at rest.

15. A system as claimed in claim 1 wherein said vibrator is operable by said control circuit in an alarm mode wherein said vibrator emits an alarm mode vibration signal having an intensity and duration so as to be perceivable by the subject to alert the subject.

16. A system as claimed in claim 1 comprising a pulse generator in said housing that emits stimulation pulses, and at least one electrode in communication with said pulse generator that delivers said stimulation pulses to cardiac tissue, and wherein said control circuit controls operation of said pulse generator dependent on said information.

17. A method for monitoring cardiac tissue comprising the steps of:
   implanting a vibrator in a subject at a first in vivo site;
   implanting a vibration sensor in the subject at a second in vivo site, separated from said first in vivo site by cardiac tissue exhibiting a tissue transfer function that represents mechanical properties of said tissue;
   emitting vibrations in vivo from said vibrator that interact with said cardiac tissue and detecting vibrations with said vibration sensor resulting from the interaction of the emitted vibrations with cardiac tissue; and
   automatically electronically analyzing the detected vibrations to derive said tissue transfer function, and to derive from said transfer function, information describing a mechanical property of the heart of the subject, selected from the group consisting of stiffness of a portion of the heart and thickness of a portion of the heart.

18. A method as claimed in claim 17 comprising emitting said vibration signal and detecting the vibrations after interaction with cardiac tissue in a procedure, and executing said procedure multiple times, separated by a plurality of heart cycles there between, and automatically electronically deriving said information based on change of said at least one mechanical property between successive executions of said procedure.

19. A method as claimed in claim 17 comprising deriving said information from a characteristic of the detected vibrations selected from the group consisting of amplitude, phase angle, energy content, and morphology.

20. A method as claimed in claim 17 comprising emitting said vibrations as a short burst, and deriving said information based on a time beginning from emission of the vibration signal to detection of the detected vibrations.

21. A method as claimed in claim 17 comprising emitting said vibration signal and detecting the vibrations after interaction with cardiac tissue only at a time when the subject is likely to be at rest.

22. A method as claimed in claim 17 comprising analyzing said information to assess a degree of congestive heart failure of the subject.

23. A method as claimed in claim 17 comprising delivering electrical stimulation pulses to the heart of the subject and controlling delivery of the stimulation pulses dependent on said information.

* * * * *